United States Patent [19]
Donovan et al.

[11] Patent Number: 5,308,775
[45] Date of Patent: May 3, 1994

[54] ASSAY DEVICES FOR CONCURRENTLY DETECTING AN ANALYTE AND CONFIRMING THE TEST RESULT

[75] Inventors: James J. Donovan, Waukegan; Stephen W. Worobec, Evanston, both of Ill.

[73] Assignee: Abbott Laboratories, Abbott Park, Ill.

[21] Appl. No.: 945,044

[22] Filed: Sep. 15, 1992

[51] Int. Cl.$^5$ ............... G01N 33/537; G01N 33/538; G01N 33/543; G01N 33/558
[52] U.S. Cl. ..................... 436/518; 422/56; 422/57; 422/58; 435/7.9; 435/7.92; 435/7.93; 435/7.94; 435/970; 435/967; 436/164; 436/169; 436/514; 436/528; 436/530; 436/805; 436/810
[58] Field of Search ................ 422/56–58; 435/7.9, 7.92, 7.93, 7.94, 970, 967; 436/518, 528, 530, 514, 164, 169, 805, 810, 824

[56] References Cited
U.S. PATENT DOCUMENTS

| | | | |
|---|---|---|---|
| 4,046,514 | 9/1977 | Johnston et al. | 422/56 |
| 4,849,338 | 7/1989 | Litman et al. | 436/810 |
| 4,900,663 | 2/1990 | Wie et al. | 435/970 |
| 5,081,013 | 1/1992 | Rovelli et al. | 435/7.92 |

OTHER PUBLICATIONS

Maggio, *Enzyme-Immunoassays*, (Boca Raton, Florida, CRC Press Inc.,), 1980.

*Primary Examiner*—David Saunders
*Assistant Examiner*—Christopher L. Chin
*Attorney, Agent, or Firm*—Gregory W. Steele; Daniel R. Curry

[57] ABSTRACT

The novel analytical devices and methods of the present invention involve dual pathway devices which provide for the confirmation of sandwich or competitive assay results. In a self-confirming sandwich assay, the labeled analyte complex becomes immobilized within a first pathway at an assay capture site to indicate the presence or amount of an analyte in the test sample. In a second pathway, a confirmatory reagent blocks the binding of the analyte or labeled analyte complex to a confirming assay site, thereby confirming that the presence of label in the assay capture site indicates a positive test sample. In a self-confirming competitive assay, a confirmed positive result is one in which the device displays a decrease in signal or no signal at the assay capture site, and the confirming assay site displays a detectable signal.

6 Claims, 1 Drawing Sheet

ASSAY DEVICES FOR CONCURRENTLY DETECTING AN ANALYTE AND CONFIRMING THE TEST RESULT

BACKGROUND OF THE INVENTION

1. Field of the Invention

In general, the present invention relates to assay methods and devices for the determination of the presence or amount of an analyte in a test sample. In particular, the invention relates to novel binding assay devices which include a means to confirm the assay result.

2. Description of Related Art

In the development of the medical diagnostics field, there has been explosive growth in the number of substances to be detected in physiological test samples. Various analytical procedures are commonly used in diagnostic assays to determine the presence and/or amount of these substances of interest or clinical significance. These clinically significant or interesting substances are referred to as analytes. Diagnostic assays have become an indispensable means for detecting analytes in test samples, and for the most part the medical profession has used highly automated clinical laboratories and sophisticated equipment for these determinations.

The ability to use materials which specifically bind to an analyte of interest has created a need for diagnostic devices based on the use of binding assays. Binding assays incorporate specific binding members, typified by antibody and antigen immunoreactants, wherein one member of the specific binding pair is labeled with a signal-producing compound (e.g., an antibody labeled with an enzyme, a fluorescent compound, a chemiluminescent compound, a radioactive isotope, a direct visual label, etc.). For example, in a binding assay the test sample suspected of containing analyte can be mixed with a labeled reagent, e.g., labeled anti-analyte antibody, and incubated for a period of time sufficient for the immunoreaction to occur. The reaction mixture is subsequently analyzed to detect either that label which is associated with an analyte/labeled reagent complex (bound labeled reagent) or that label which is not complexed with analyte (free labeled reagent). As a result, the amount of free or bound label can be correlated to the amount of analyte in the test sample.

The solid phase assay format is a commonly used binding assay technique. There are a number of assay devices and procedures wherein the presence of an analyte is indicated by the analyte's binding to a labeled reagent and an immobilized or insoluble complementary binding member. The immobilized binding member is bound, or becomes bound during the assay, to a solid phase such as a dipstick, teststrip, flow-through pad, paper, fiber matrix or other suitable solid phase material. The binding reaction between the analyte and the assay reagents results in a distribution of the labeled reagent between that which is immobilized upon the solid phase and that which remains free. The presence or amount of analyte in a test sample is typically indicated by the extent to which the labeled reagent becomes immobilized upon the solid phase material.

The use of reagent-impregnated teststrips in specific binding assays is well-known. In such procedures, a test sample is applied to one portion of the teststrip and is allowed to migrate or wick through the strip material. Thus, the analyte to be detected or measured passes through or along the material, possibly with the aid of an eluting solvent which can be the test sample itself or a separately added solution. The analyte migrates into a capture or detection zone on the teststrip, wherein a complementary binding member to the analyte is immobilized. The extent to which the analyte becomes bound in the detection zone can be determined with the aid of the labeled reagent which can also be incorporated in the teststrip or which can be applied separately.

An early teststrip device is described by Deutsch, et al. in U.S. Pat. No. 4,361,537. In general, the device comprises a material capable of transporting a solution by capillary action, i.e., a wicking or chromatographic action. Different areas or zones in the teststrip contain the assay reagents needed to produce a detectable signal as the analyte is transported to or through such zones. The device is suited for both chemical assays and binding assays and uses a developer solution to transport analyte along the strip.

Many alternatives to or variations on the Deutsch, et al. device have been disclosed. For example, Grubb, et al. (U.S. Pat. No. 4,168,146) describe the use of a porous teststrip material to which is covalently bound an antigen-specific antibody. In performing the assay, the teststrip is immersed in a solution suspected of containing an antigen, and capillary migration of the solution through the teststrip is allowed to occur. As the antigen moves through the teststrip it binds to the immobilized antigen-specific antibody. The presence of antigen is then determined by wetting the teststrip with a second antigen-specific antibody to which a fluorescent or enzyme label is covalently bound. Quantitative testing can be achieved by measuring the length of the strip that contains bound and labeled antigen.

Weng, et al. (U.S. Pat. No. 4,740,468) describe another device and method for performing a specific binding assay. The assay involves both an immobile second binding member which binds to a mobile first binding member and an immobilized analog of the analyte which removes unbound first binding member from the assay system prior to its contacting the detection site. Greenquist, et al. (U.S. Pat. No. 4,806,311) describe a similar device wherein a first immobilized reagent, such as an analyte-analog, is present in a reagent zone to remove free monovalent labeled-binding members from the assay system prior to the test samples contact with the detection layer reagents.

Analyte detection in a specific binding assay can be achieved using either a sandwich assay or competitive assay format. The confirmation of the assay result is typically accomplished by treating the test sample to neutralize the analyte and then repeating the assay. This process involves several additional procedural steps and reagent additions by the user and subjects the assays to an increased risk of error. If the initial assay result is not confirmed, the initial positive result may be falsely positive, thereby leading to errors in diagnosis and treatment. Thus, there is a need for a specific binding assay format and device which permit the simultaneous confirmation of the assay result without the need for additional operations.

SUMMARY OF THE INVENTION

The present invention involves a self-performing confirmatory assay device which can be constructed to perform a sandwich assay or a competitive assay. A sandwich assay device includes a solid phase having at least two separate fluid-flow pathways, wherein a first pathway contains an assay capture site and a second pathway contains both a confirmatory reagent and a confirming assay site. The first and second pathways may be two individual pieces of porous material or two separate portions of a single porous material. A specific binding member, which directly or indirectly binds a labeled analyte complex, is immobilized both in the first pathway at the assay capture site and in the second pathway at the confirming assay site. The device further contains a confirmatory reagent involving an unlabeled specific binding member which binds the analyte and inhibits the binding of the analyte or labeled analyte complex in the confirming assay site. Optionally, the device includes the labeled reagent, which directly or indirectly binds analyte, thereby forming the labeled analyte complex. Preferably, the confirmatory reagent is selected from a different source or species than the labeled or immobilized binding reagents.

When the test sample is contacted to the device, the labeled analyte complex becomes immobilized within the first pathway at the assay capture site to indicate the presence or amount of an analyte in the test sample. In the second pathway, the confirmatory reagent blocks the binding of the analyte or labeled analyte complex to the conforming assay site, thereby confirming that the presence of label in the assay capture site indicates a positive test sample.

An exemplary competitive assay device includes a solid phase having at least a first and a second separate fluid-flow pathways. The first pathway contains an assay capture site, and the second pathway contains both a confirmatory reagent and a confirming assay site. An immobilized specific binding member, which competes with the analyte for binding a labeled reagent, results in the binding of the labeled reagent in inverse proportion to the presence or amount of the analyte in the test sample. The binding member is immobilized both in the first pathway at the assay capture site and in the second pathway at the confirming assay site. The device further contains a confirmatory reagent comprising an unlabeled specific binding member which blocks the binding of the analyte in the confirming assay site. The test sample is contacted to the device, and a confirmed positive result is one in which the device displays a decrease in signal or no signal at the assay capture site whereas the confirming assay site displays a detectable signal.

DETAILED DESCRIPTION OF THE INVENTION

Figure 2:
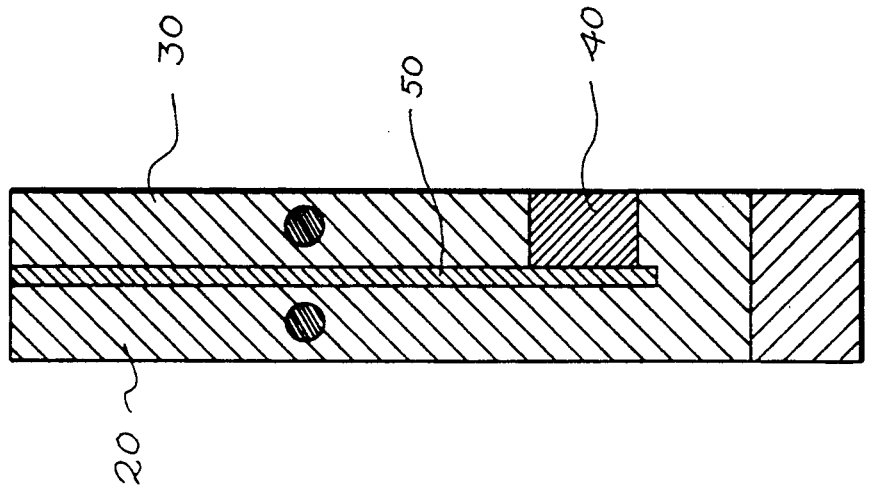
FIG. 2 depicts an alternative embodiment of the present invention involving a teststrip-type device having two fluid-flow pathways, in a single piece of porous material, wherein the pathways are separated by a barrier.

Typically, the confirmation of a positive assay result requires that the assay be repeated. The novel binding assay devices of the present invention provide a means by which a confirmatory assay is performed essentially automatically and simultaneously with an assay for the detection of analyte.

In the present invention, the confirming reagent is a material that specifically competes with or inhibits the binding of the analyte to the solid phase or to the label, thereby interfering with the separation or detection of the analyte. For example, to confirm a positive result in an assay for Hepatitis B surface antigen (HBsAg), antibodies to HBsAg are added to the test sample as the confirming reagent, and the assay is performed using the treated test sample. The added antibody specifically binds to the HBsAg in the sample, and blocks the binding of the test sample antigen to another anti-HBsAg antibody immobilized on a solid phase. As a consequence, the positive test sample now provides a negative result in the confirmatory assay. If the result of the confirmatory assay is still positive, it indicates that the original positive is "non-neutralizable" and is a non-specific positive, i.e., the positive result in the original assay is due to the nonspecific binding of some material other than the analyte.

For a confirmatory assay to be dependable, some or all of the confirming reagents should be different from those used in the original assay. For example, in a sandwich assay the confirming reagent should be from a different source or species than the labeled or immobilized binding reagents used in the detection assay. The use of a different binding member helps to ensure that any nonspecific binding that may arise from the interaction of the test sample with the reagents does not occur in both the detection assay and the confirmatory assay. In general, the confirming reagent should either be obtained from a different species (e.g. human vs. animal), be produced from a different source (e.g. viral antigen vs. recombinant) or be purified by a different method (e.g. electrophoresis vs. chromatography) than the reagents used in the original assay.

Before proceeding with the description of the various embodiments of the present invention, a number of terms used herein will be defined.

"Test sample" refers to a material suspected of containing the analyte. The test sample can be used directly as obtained from the source or after pretreatment so as to modify its character. The test sample can be derived from any source, such as a physiological fluid, including, blood, saliva, ocular lens fluid, cerebral spinal fluid, sweat, urine, milk, ascites fluid, mucous, synovial fluid, peritoneal fluid, amniotic fluid or the like. The test sample can be pretreated prior to use, such as preparing plasma from blood, diluting viscous fluids, or the like; methods of treatment can involve filtration, distillation, concentration, inactivation of interfering components, and the addition of reagents. Besides physiological fluids, other liquid samples can be used such as water, food products and the like for the performance of environmental or food production assays. In addition, a solid material suspected of containing the analyte can be used as the test sample once it is modified to form a liquid medium or to release the analyte.

"Specific binding member" refers to a member of a specific binding pair, i.e., two different molecules wherein one of the molecules specifically binds to the second molecule through chemical or physical means. In addition to antigen and antibody specific binding pair members, other specific binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogs of the original specific binding member, for example an analyte-analog or a specific binding member made by recombinant techniques or molecular engineering. If the specific binding member is an immunoreactant it can be, for example, an antibody, antigen, hapten, or complex thereof, and if an antibody is used, it can be a monoclonal or polyclonal antibody, a recombinant protein or antibody, a chimeric antibody, a mixture(s) or fragment(s) thereof, as well as a mixture of an antibody and other specific binding members. The details of the preparation of such antibodies and their suitability for use as specific binding members are well-known to those skilled-in-the-art.

"Analyte" or "analyte of interest" refers to the compound or composition to be detected or measured, which has at least one epitope or binding site. The analyte can be any substance for which there exists a naturally occurring analyte-specific binding member or for which an analyte-specific binding member can be prepared. Analytes include, but are not limited to toxins, organic compounds, proteins, peptides, microorganisms, amino acids, nucleic acids, hormones, steroids, vitamins, drugs (including those administered for therapeutic purposes as well as those administered for illicit purposes), and metabolites of or antibodies to any of the above substances. The term "analyte" also includes any antigenic substances, haptens, antibodies, macromolecules and combinations thereof.

"Analyte-analog" refers to a substance which cross-reacts with the analyte-specific binding member, although it may do so to a greater or a lesser extent than does the analyte itself. The analyte-analog can include a modified analyte as well as a fragmented or synthetic portion of the analyte molecule, so long as the analyte-analog has at least one epitopic site in common with the analyte of interest. An example of an analyte-analog is a synthetic peptide sequence which duplicates at least one epitope of the whole-molecule analyte so that the analyte-analog can bind to the analyte-specific binding member.

"Labeled reagent" refers to a substance comprising a detectable label attached to a specific binding member. The attachment may be covalent or non-covalent binding, but the method of attachment is not critical to the present invention. The label allows the labeled reagent to produce a detectable signal that is directly or indirectly related to the amount of analyte in the test sample. The specific binding member component of the labeled reagent is selected to directly bind to the analyte or to indirectly bind the analyte by means of an ancillary specific binding member, which is described in greater detail hereinafter. The labeled reagent can be incorporated into the test device, it can be combined with the test sample to form a test solution, it can be added to the device separately from the test sample or it can be predeposited or reversibly immobilized at the capture site. In addition, the binding member may be labeled before or during the performance of the assay by means of a suitable attachment method.

"Label" refers to any substance which is capable of producing a signal that is detectable by visual or instrumental means. Various labels suitable for use in the present invention include labels which produce signals through either chemical or physical means. Such labels can include enzymes and substrates; chromogens; catalysts; fluorescent compounds; chemiluminescent compounds; radioactive labels; direct visual labels including colloidal metallic particles such as gold, colloidal non-metallic particles such as selenium, dyed or colored particles such as a dyed plastic or a stained microorganism, organic polymer latex particles and liposomes or other vesicles containing directly visible substances; and the like.

The selection of a particular label is not critical to the present invention, but the label will be capable of generating a detectable signal either by itself, such as a visually detectable colored organic polymer latex particle, or instrumentally detectable, such as a fluorescent compound, or detectable in conjunction with one or more additional signal producing components, such as an enzyme/substrate signal producing system. A variety of different labeled reagents can be formed by varying either the label or the specific binding member component of the labeled reagent; it will be appreciated by one skilled-in-the-art that the choice involves consideration of the analyte to be detected and the desired means of detection.

"Signal producing component" refers to any substance capable of reacting with another assay reagent or with the analyte to produce a reaction product or signal that indicates the presence of the analyte and that is detectable by visual or instrumental means. "Signal production system", as used herein, refers to the group of assay reagents that are needed to produce the desired reaction product or signal. One or more signal producing components can be reacted with the label to generate a detectable signal. For example, when the label is an enzyme, amplification of the detectable signal is obtained by reacting the enzyme with one or more substrates or additional enzymes and substrates to produce a detectable reaction product.

In an alternative signal producing system, the label can be a fluorescent compound where no enzymatic manipulation of the label is required to produce the detectable signal. Fluorescent molecules such as fluorescein, phycobiliprotein, rhodamine and their derivatives and analogs are suitable for use as labels in such a system.

In a preferred embodiment of the present invention, a visually detectable label is used as the label component of the labeled reagent, thereby providing for the direct visual or instrumental readout of the presence or amount of the analyte in the test sample without the need for additional signal producing components at the detection sites. Suitable materials for use are colloidal metals, such as gold, and dye particles as disclosed in U.S. Pat. Nos. 4,313,734 and 4,373,932. Non-metallic colloids, such as colloidal selenium, tellurium and sulfur particles may also be used and are disclosed in U.S. Pat. No. 4,954,452.

"Immobilized reagent" refers to a specific binding member that is attached within or upon a portion of the solid phase support or chromatographic strip to form a capture or detection site wherein the analyte and/or labeled reagent become immobilized on the strip or wherein the immobilized reagent slows the migration of the analyte and/or labeled reagent through the strip. The method of attachment is not critical to the present invention. The capture reagent facilitates the observation of the detectable signal by substantially separating the analyte and/or the labeled reagent from unbound assay reagents and the remaining components of the test sample. Typically, the immobilized reagent is selected to bind the analyte, the labeled reagent or a complex thereof. In preferred embodiments, the immobilized reagent binds to the analyte for the completion of a sandwich complex. The immobilized reagent may be chosen to directly bind the analyte or indirectly bind the analyte by means of an ancillary specific binding member which is bound to the analyte. In addition, the immobilized reagent may be immobilized on the solid phase before or during the performance of the assay by means of any suitable attachment method.

Typically, the immobilized reagents of the present invention are in a delimited or defined portion of the solid phase support such that the specific binding reaction between the immobilized reagent and analyte is localized or concentrated in a delimited site. This facilitates the detection of label that is immobilized at the capture site in contrast to other portions of the solid phase support. The delimited site is typically less than 50% of the solid phase support, and preferably less than 10% of the solid phase support. The immobilized reagent can be applied to the solid phase material by dipping, inscribing with a pen, dispensing through a capillary tube or through the use of reagent jet-printing or any other suitable dispensing techniques. In addition, the capture site can be marked, for example with a dye, such that the position of the capture site upon the solid phase material can be visually or instrumentally determined even when there is no label immobilized at the site. Preferably, the immobilized reagent is positioned on the strip such that the capture site is not directly contacted with the test sample, that is, the test sample must migrate by capillary action through at least a portion of the strip before contacting the immobilized reagent.

The immobilized reagent may be provided in a single capture or detection site or in multiple sites on or in the solid phase material. The immobilized reagent may also be provided in a variety of configurations to produce different detection or measurement formats. Alternatively, the immobilized reagent can be distributed over a large portion of the solid phase material in a substantially uniform manner to form the capture site. The extent of signal production in the capture site is related to the amount of analyte in the test sample.

"Ancillary specific binding member" refers to any member of a specific binding pair which is used in the assay in addition to the specific binding members of the labeled reagent or immobilized reagent. One or more ancillary specific binding members can be used in an assay. For example, an ancillary specific binding member can be capable of binding the labeled reagent to the analyte of interest in instances where the analyte itself could not directly attach to the labeled reagent. The ancillary specific binding member can be incorporated into the assay device or it can be added to the device as a separate reagent solution.

To avoid unnecessary repetition, the following confirmatory assays will be described as involving teststrip-type devices although many solid phase assay formats based upon the teachings of the present invention will become apparent to those skilled-in-the-art. The required element is that the self-confirming aspect of the assay occur essentially simultaneously with the detection assay and serve to eliminate unconfirmed positive assay results.

It will be appreciated by one skilled-in-the-art that a teststrip device can be made of more than one material (e.g., different zones, portions, layers, areas or sites can be made of different materials) so long as the multiple materials are in fluid-flow contact with one another thereby enabling the passage of test sample between the materials. Fluid-flow contact permits at least some components of the test sample, e.g., analyte, to pass between the zones of the device, and fluid-flow is preferably uniform along the contact interface between the different zones.

The self-confirming assay devices of the present invention differ from conventional teststrips in that the devices of the present invention contain at least two distinct pathways through which the test sample migrates. The two paths may be parallel strips of porous material or two separate regions of a single piece of porous material. In the later instance, the two separate regions may be physically separated by a barrier means. Any suitable barrier means may be used, such as an etched channel, a nonporous barrier, a hydrophobic barrier, etc.

The novel assay devices of the present invention involve at least one capture site or detection site in a first pathway and at least one confirmatory site in a second pathway. For example, in a sandwich assay for the detection of antibody to Hepatitis B core antigen, a teststrip detection site is incorporated into a first pathway by immobilizing Hepatitis B core antigen in the site. A test solution is made by combining the test sample with a labeled Hepatitis B core antigen. The test solution may be formed in the teststrip device itself or in a separate container. The labeled antigen binds to the antibody present in the test sample, the test solution migrates through the first pathway and contacts the detection site. A detectable signal appears at the detection site due to the capture of the labeled complex by the immobilized antigen. A second set of reactions simultaneously occur in a second pathway containing immobilized Hepatitis B core antigen in the confirmatory site. This pathway includes a mobile confirmatory reagent, such as unlabeled Hepatitis B core antigen, positioned in the pathway in a site preceding the confirmatory site. The binding of the unlabeled HBsAg to the analyte antibody inhibits the binding of the analyte in the confirmatory site. A confirmed positive result is one in which the device displays a detectable signal at the capture site and no detectable signal at the confirming site.

In an example of a competitive assay for the detection of antibody to HBsAg, the capture site in the first pathway is incorporated with immobilized antibody to HBsAg, and the labeled reagent is labeled HBsAg. The test sample antibody and immobilized reagent compete in binding to the labeled reagent, thereby inhibiting the binding of the labeled reagent to the immobilized reagent. The result is a decrease in detectable signal at the capture site as the analyte concentration increases.

To confirm the competitive assay, it is necessary to remove the analyte from the test solution. This may be accomplished by attaching an analyte-specific binding member as the confirming reagent to the teststrip at a position where the test solution contacts the confirming reagent prior to contacting the immobilized antibody at the confirmation site. The confirming reagent removes the analyte from the test solution such that the labeled reagent is able to bind at the confirmation site without competition. A confirmed positive result is one in which the device shows a decrease in signal or no signal at the capture site relative to a control, and the confirming site displays a detectable signal.

ASSAY DEVICES

While the methods and devices of the present invention may be applied to any suitable specific binding pairs, the following examples will typically refer to antibody/antigen specific binding pairs in order to simplify the description.

Figure 1:
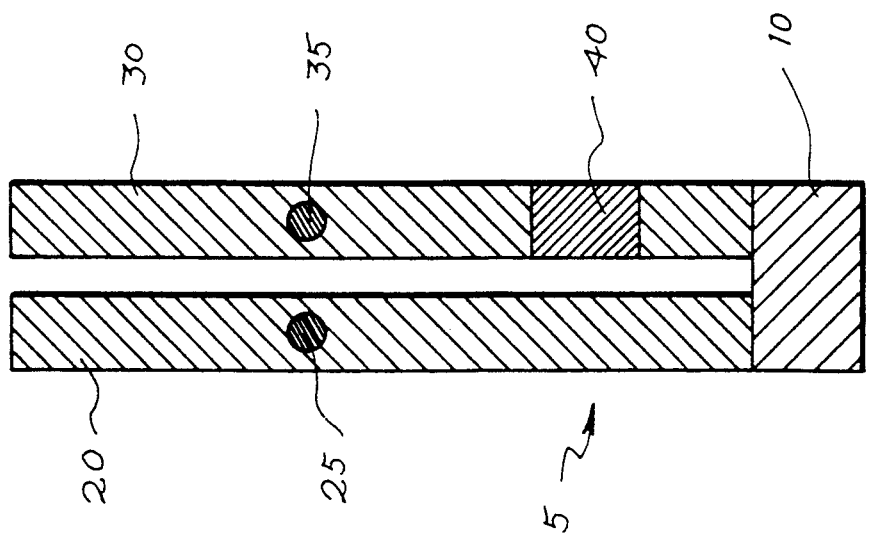
FIG. 1 depicts one embodiment of the present invention involving a teststrip-type device having two fluid-flow pathways formed from two pieces of porous material.

One embodiment of the present invention involves a self-performing sandwich assay/confirmatory device (5) as illustrated in FIG. 1. Typically, a mixture is formed by contacting the test sample suspected of containing the analyte (Ag) with a predetermined amount of labeled anti-analyte antibody (Ab*). The labeled antibody may be separate from or incorporated within the test device. For example, the labeled antibody may be incorporated within the test sample application site (10). The mixture migrates through the two, distinct teststrip pathways (20 and 30). In the first pathway (20), the reaction mixture contacts an assay capture site (25) containing an immobilized analyte-specific antibody (|-Ab) that is capable of binding to the Ag-Ab* complex to form an immobilized |-Ab-Ag-Ab* complex that is detectable at the capture site. In the second pathway (30), the mixture first contacts a reagent zone (40) containing a confirming reagent, such as an unlabeled anti-analyte antibody (Ab). The unlabeled antibody is capable of binding to the Ag-Ab* complex to form a mobile Ab-Ag-Ab* complex. The mixture is then transported to the confirmatory assay site (35). The confirmatory site contains an immobilized analyte-specific antibody (|-Ab) that is capable of binding to the antigen. The confirming reagent, however, inhibits or prevents such a binding reaction, and as a result, no detectable complex is immobilized at the confirmatory assay capture site (35). The lack of a detectable signal in the confirmatory site in the second pathway confirms that the occurrence of the positive test result (i.e., detectable signal) in the first pathway is due to the presence of the analyte in the test sample.

An alternative device embodiment is illustrated in FIG. 2 involving a multi-element teststrip device. In this embodiment, the first pathway (20) and second pathway (30) are separated by a barrier means (50).

Yet another embodiment of the present invention involves a device for the performance of an antibody/antigen competitive assay. A reaction mixture is formed by contacting the test sample suspected of containing the analyte (Ab) with a predetermined amount of labeled antigen (Ag*). The labeled antigen may be separate from or incorporated within the test device. The reaction mixture migrates through the two, distinct teststrip pathways or channels. In the first pathway, the reaction mixture contacts a capture site containing an immobilized anti-antigen antibody (|-Ab) that is capable of competing with the analyte in binding to the labeled antigen. The binding reaction forms an immobilized |-Ab-Ag* complex which is detectable at the capture site. The more analyte present in the test sample the less signal is displayed at the capture site because the Ab-Ag* complex is formed. In the second pathway, the mixture first contacts a confirming reagent, such as an unlabeled, immobilized antigen (|-Ag). The immobilized antigen is capable of binding to the antibody analyte, thereby separating the analyte from the mixture. The mixture then migrates to the confirmatory site containing an immobilized anti-antigen antibody (|-Ab) that is capable of binding to the free labeled antigen. As a result, a detectable complex is immobilized at the confirmatory site in the second pathway. The occurrence of detectable signal at the confirmatory site in the second pathway confirms that the positive test result (i.e., lack of detectable signal) at the capture site in the first pathway is due to the presence of the analyte of interest in the test sample.

The teststrip devices of the present invention may optionally include a premixing application pad, wherein the pad contains the labeled reagent. The material of the application pad should be chosen for its ability to mix the test sample with the assay reagents as well as absorb a quantity of test sample at a faster rate than does the porous strip material. If nitrocellulose is used as the porous material, then a hydrophilic polyethylene material or a glass fiber filter paper are suitable application pad materials. Other reagents which can be contained in the application pad include, but are not limited to, the confirming reagent (if separate pads are used for each pathway), ancillary specific binding members, test sample pretreatment reagents and signal producing components. The isolation of reagents in the application pad also keeps interactive reagents separate and facilitates the manufacturing process.

An application pad can be made of any material from which the test sample can pass to the porous material containing the capture site. Materials preferred for use in the application pad include porous polyethylene materials or pads, glass fiber pads or filter paper. The material must also be chosen for its compatibility with the analyte and assay reagents.

The particular dimensions of the teststrip will be a matter of convenience and will depend upon the size of the test sample involved, the assay protocol, the label detection means, the measurement means, and the like. For example, the dimensions may be chosen to regulate the rate of fluid migration as well as the amount of test sample to be imbibed by the porous material.

It is also within the scope of this invention to have a reagent, at the distal end of a teststrip device, which indicates the completion of a binding assay (i.e., an end of assay indicator). For example, the end of the assay may be shown by the indicator's changing color upon contact with the test solution, wicking solution or a signal producing component. Reagents which would change color upon contact with an aqueous test solution include the dehydrated transition metal salts, such as $CuSO_4$, $Co(NO_3)_2$, and the like. The pH indicator dyes can also be selected to respond to the pH of the buffered wicking solution. For example, phenolphthalein changes from clear to intense pink upon contact with a wicking solution having a pH range between 8.0–10.0.

In yet another embodiment, the device can include an absorption means downstream from the capture site or sites. It will be appreciated that the absorption means can serve to increase the amount of test sample which passes through the capture site on the porous material. The absorption means may consist of an extended length of the porous material. Preferably the absorption means consists of a quantity of an additional absorbent material.

When small quantities of non-aqueous or viscous test samples are applied to the device, it may be necessary to employ a wicking solution, preferably a buffered wicking solution, to facilitate the travel of the reagent(s) and test sample through the device. When an aqueous test sample is used, a wicking solution generally is not necessary but can be used to improve flow characteristics or adjust the pH of the test sample.

The confirming reagent may be in the test sample application site or in any portion of the pathway that is upstream of the confirmatory site. By incorporating all of the reagents into or on the test device, the assay is substantially self-performing once the test sample is contacted to the device. In those assay methods involving a label which is not detectable by itself, the porous material is also contacted to any remaining members of a signal producing system that were not included with the test solution or were not present on the porous material.

It will be appreciated by those skilled-in-the-art that the concepts of the present invention are applicable to various types of assay configurations, analytes, labels and solid phase materials. Thus, many other signal producing assays to which the present inventive concepts can be applied. The embodiments described and the alternative embodiments presented are intended as examples, rather than as limitations, of assay devices containing a self-confirming assay component. Thus, the description of the invention is not intended to limit the invention to the particular embodiments disclosed, but it is intended to encompass all equivalents and subject matter within the scope of the invention as described above and as set forth in the following claims.

What is claimed is:

1. A self-performing confirmatory assay device for assaying an analyte in a test sample and for confirming a positive assay result involving a sandwich assay format comprising:
   a) a solid phase having at least a first and a second separate fluid-flow pathways, wherein said first pathway contains an assay capture site, and wherein said second pathway contains both a mobile confirmatory reagent and a confirming assay site located downstream from said mobile confirmatory reagent;
   b) an optional application pad in fluid contact with said first and second fluid flow pathways;
   c) a specific binding member, which directly or indirectly specifically binds a labelled analyte complex formed by direct or indirect specific binding of a labelled reagent with said analyte, wherein said labelled reagent is optionally incorporated either within said application pad or in said first and second pathways, and said specific binding member is immobilized both in said first pathway at said assay capture site and in said second pathway at said confirming assay site; and
   d) said confirmatory reagent comprising an unlabelled specific binding member which becomes mobile when contacted with said test sample and specifically binds to said analyte and thereby inhibits the binding of said analyte or said labelled analyte complex with said specific binding member immobilized in said confirming assay site.

2. The device according to claim 1, wherein said first and second pathways comprise a porous material wherein said labeled reagent is contained in at least one reagent zone upstream from said assay capture site in said first pathway and wherein said labeled reagent and said confirmatory reagent are contained in at least one reagent zone upstream from said confirming assay site in said second pathway.

3. The device according to claim 2, wherein said first and second pathways comprise two individual pieces of porous material.

4. The device according to claim 2, wherein said first and second pathways comprise two separate portions of a single porous material.

5. The device according to claim 1, wherein said confirmatory reagent is from a different source or species than the labelled or immobilized binding reagents.

6. A self-performing confirmatory assay for an analyte in a test sample involving a sandwich assay format, comprising the steps of:
   a) providing a device comprising
      i) a solid phase having at least a first and a second separate fluid-flow pathways, wherein said first pathway contains an assay capture site, and wherein said second pathway contains both a mobile confirmatory reagent and a confirming assay site located downstream from said mobile confirmatory reagent;
      ii) an optional application pad in fluid contact with said first and second fluid flow pathways;
      iii) a specific binding member, which directly or indirectly specifically binds a labelled analyte complex formed by direct or indirect specific binding of a labelled reagent with an analyte in said test sample, wherein said labelled reagent is optionally incorporated either within said application pad or in said first and second pathways, and said specific binding member is immobilized both in said first pathway at said assay capture site and in said second pathway at said confirming assay site;
      iv) said mobile confirmatory reagent comprising an unlabelled specific binding member which specifically binds to said analyte and inhibits the binding of said analyte or said labelled analyte complex with said specific binding member immobilized in said confirming assay site;
   b) contacting said test sample with said labelled reagent if said labelled reagent is not incorporated in said device to form a reaction mixture and contacting said reaction mixture with the device, or contacting the test sample with said device if said labelled reagent is incorporated in said device; and
   c) detecting a signal producing label from said labelled reagent, wherein when said signal producing label is an enzyme, a substrate is subsequently allowed to contact said enzyme, and wherein said labelled analyte complex that is immobilized within said first pathway at said assay capture site is related to the presence or amount of said analyte in the test sample, and wherein said confirmatory reagent prevents the binding of said analyte or said labelled analyte complex with said specific binding member immobilized in said confirming assay site, thereby confirming that signal displayed by said assay capture site indicates a positive test sample.

* * * * *

UNITED STATES PATENT AND TRADEMARK OFFICE
CERTIFICATE OF CORRECTION

PATENT NO. : 5,308,775

DATED : May 3, 1994

INVENTOR(S) : James J. Donovan, Stephen W. Worobec

It is certified that error appears in the above-identified patent and that said Letters Patent is hereby corrected as shown below:

Column 8, line 44

Delete "HBsAg" and insert --Hepatitis B core antigen--

Signed and Sealed this

Thirteenth Day of December, 1994

Attest:

BRUCE LEHMAN

Attesting Officer

Commissioner of Patents and Trademarks